(12) United States Patent
Armstrong et al.

(10) Patent No.: US 12,033,756 B2
(45) Date of Patent: *Jul. 9, 2024

(54) SYSTEMS AND METHODS FOR TREATMENT SELECTION

(71) Applicant: AIFRED HEALTH, Montreal (CA)

(72) Inventors: Caitrin Armstrong, Montreal (CA); David Benrimoh, Montreal (CA); Robert Fratila, Montreal (CA); Adam Kapelner, Montreal (CA); Akiva Kleinerman, Montreal (CA); Joseph Mehltretter, Montreal (CA); Ariel Rosenfeld, Montreal (CA)

(73) Assignee: AIFRED HEALTH, Montreal (CA)

( * ) Notice: Subject to any disclaimer, the term of this patent is extended or adjusted under 35 U.S.C. 154(b) by 209 days.

This patent is subject to a terminal disclaimer.

(21) Appl. No.: 17/493,070

(22) Filed: Oct. 4, 2021

(65) Prior Publication Data
US 2022/0037023 A1 Feb. 3, 2022

Related U.S. Application Data

(63) Continuation of application No. PCT/CA2021/050446, filed on Apr. 1, 2021.
(Continued)

(51) Int. Cl.
*G16H 50/20* (2018.01)
*G06F 9/445* (2018.01)
(Continued)

(52) U.S. Cl.
CPC ............ *G16H 50/20* (2018.01); *G06N 5/022* (2013.01); *G06N 20/00* (2019.01); *G16H 10/20* (2018.01);
(Continued)

(58) Field of Classification Search
CPC ........ G16H 50/20; G16H 10/60; G16H 50/70; G16H 20/10; G16H 10/20; G16H 20/70; G06N 20/00; G06N 5/022
See application file for complete search history.

(56) References Cited

U.S. PATENT DOCUMENTS 9,764,136 B2 *  9/2017  McIntyre ............... G16H 50/20
11,605,463 B2 *  3/2023  Armstrong ............. G16H 50/20
(Continued)

FOREIGN PATENT DOCUMENTS

AU      2018277256 A1    1/2020
CA        2715825 A1    8/2009
(Continued)

OTHER PUBLICATIONS

International Search Report and Written Opinion issued in corresponding application No. PCT/CA2021/050446 dated Jul. 2, 2021.
(Continued)

*Primary Examiner* — Thuy Dao
(74) *Attorney, Agent, or Firm* — BCF LLP

(57) ABSTRACT

There is disclosed a method and a system for predicting the efficacy of one or more treatments. A completed questionnaire may be received from a patient requiring treatment. The responses to the questionnaire may be input to a machine learning algorithm (MLA). The MLA may have been trained using labelled patient data. A predicted efficacy of one or more treatments and a prototype corresponding to the patient may be received from the MLA. An interface may be output indicating the predicted efficacy of the one or more treatments and the prototype.

20 Claims, 9 Drawing Sheets

Related U.S. Application Data

(60) Provisional application No. 63/079,161, filed on Sep. 16, 2020, provisional application No. 63/004,720, filed on Apr. 3, 2020.

(51) Int. Cl.
| | |
|---|---|
| *G06F 9/455* | (2018.01) |
| *G06N 5/02* | (2023.01) |
| *G06N 5/022* | (2023.01) |
| *G06N 20/00* | (2019.01) |
| *G06Q 40/08* | (2012.01) |
| *G16H 10/20* | (2018.01) |
| *G16H 10/60* | (2018.01) |
| *G16H 20/10* | (2018.01) |
| *G16H 20/70* | (2018.01) |
| *G16H 50/70* | (2018.01) |

(52) U.S. Cl.
CPC ............ *G16H 10/60* (2018.01); *G16H 20/10* (2018.01); *G16H 20/70* (2018.01); *G16H 50/70* (2018.01)

(56) References Cited

U.S. PATENT DOCUMENTS

| | | |
|---|---|---|
| 2014/0052474 A1 | 2/2014 | Madan et al. |
| 2018/0232486 A1 | 8/2018 | Carpenter et al. |
| 2019/0267112 A1 | 8/2019 | Taliaz |
| 2019/0341152 A1 | 11/2019 | Mellem et al. |

FOREIGN PATENT DOCUMENTS

| | | |
|---|---|---|
| CN | 110383389 A | 10/2019 |
| WO | 2017210502 A1 | 12/2017 |

OTHER PUBLICATIONS

Supplementary European Search Report issued in co-pending European patent application No. 21781328.6 on Apr. 24, 2024.

\* cited by examiner

| PROTOTYPE | DISTANCE [0,1] | EXPLANATION (INFLUENTIAL FEATURES) |
|---|---|---|
| PROTOTYPE A | 0.2 | BOB DOES NOT HAVE THE FOLLOWING FEATURES: DECREASED WEIGHT, LOW ENERGY |
| PROTOTYPE B | 0.5 | BOB IS HIGHLY EDUCATED BUT IS NOT ANXIOUS |
| PROTOTYPE A | 0.8 | BOB'S MOOD VARIATION AND INTERPERSONAL SENSITIVITY |

PATIENTS     DR. FULL NAME

< ALL PATIENTS
CHARLOTTE JENKINS | 28 - FEMALE | ID: 123456789 (CLINICAL TRIAL)     PATIENT MENU ≡

CLINICAL ALGORITHM TREATMENT_SELECTION

< BACK

TREATMENT SELECTION     COLORS ⓘ

YOU HAVE ENTERED THE FINAL STEP OF THE TREATMENT ALGORITHM WITH THIS PATIENT. AT THIS POINT THE GUIDELINE-INFORMED PRACTIVE IS TO OPTIMISE THE DOSE OF ANY ANTIDEPRESSANTS OR AUGMENTING AGENTS. IF AN AUGMENTING AGENT HAS NOT YET BEEN ADDED, THE GUIDELINE-INFORMED PRACTICE IS TO ADD ONE OF THE FOLLOWING AUGMENTATION TREATMENTS LISTED IN YELLOW. WE HAVE LSITED THESE IN ORDER OF THEIR LEVEL OF EVIDENCE OF EFFECTIVENESS ACCORDING TO THE CANMAN 2016 GUIDELINES, AND ALSO KEEPING IN MIND TOLERABILITY. OTHER THERAPIES, SUCH AS sTMS, ECT, PSYCHOTHERAPY, AS WELL AS REFERRALTO A SPECIALIST SHOULD BE CONSIDERED IF THEY HAVE NOT BEEN ALREADY.

SELECTED TREATMENTS (5)
- PAROXETINE CR   10 mg
- LORAZEPAM   15 mg
- VENLAFAXINE (XR) 75 mg
- ESCITALOPRAM   5 mg
- SERTRALINE   15 mg

TREATMENTS LIST   ( 🔍 FIND OTHER TREATMENTS )

| TREATMENT | FREQUENCY | DOSAGE | SELECTED |
|---|---|---|---|
| PAROXETINE CR (ANTIDEPRESSANT FIRST LINE) | qd | 10 mg ▼ | ☑ |

*ALPHA2-ADRENERGIC AGONIS 5-HT2 ANTAGONIST*
TYPICAL DOSE INCREASE: 5 mg
EFFECTIVE DOES RANGE: 10 - 20 mg
MIN & MAX DOSE RANGE: 40 - 100 mg
DOSING TIPS: *START AT 10 mg qd*

CLINICAL PEARLS: •HELPFUL FOR INSOMNIA (CANMAT LEVEL 2) BECAUSE IT IS SEDATING. •KNOWN TO STIMULATE APPETITE AND CAN CAUSE WEIGHT GAIN. •VERY LOW RATES OF SEXUAL DYSFUNCTION COMPARED WITH OTHER ANTIDEPRESSANTS.

*34.14% PROBABILITY OF REMISSSION, WHICH REPRESENTS A DIFFERENCE OF 3.71% COMPARED TO THE – LESS PATIENT'S MEAN PROBABILITY OF REMISSION ACROSS ALL PREDICTED TREATMENTS.*
THE PATIENT'S MEAN PROBABILITY OF REMISSION ACROSS PREDICTED TREATMENTS IS 30.43%. THE POPULATION BASELINE PROBABILITY OF REMISSION IS 34.85%.
IMPORTANT VARIABLES:
INCREASED APPETITE;
SYMPATHETIC AROUSAL;
EARLY MORNING INSOMNIA;

| CLOMIPRAMINE (ANTIDEPRESSANT SECOND-THIRD LINE) | qHS | 25 mg ▼ | ☐ |

*TCA*
TYPICAL DOSE INCREASE: 25 mg
EFFECTIVE DOES RANGE: 100 - 250 mg
MIN & MAX DOSE RANGE: 40 - 100 mg

CLINICAL PEARLS: •ANTICHOLINERGIC SIDE-EFFECTS ARE COMMON. •CAN PROLONG QTc INTERVAL. •CAN BE FATAL IN OVERDOSE.

*34.14% PROBABILITY OF REMISSSION, WHICH REPRESENTS A DIFFERENCE OF 3.71% COMPARED TO THE + MORE PATIENT'S MEAN PROBABILITY OF REMISSION ACROSS ALL PREDICTED TREATMENTS.*

| VENLAFAXINE (XR) (ANTIDEPRESSANT FIRST LINE) | qd | 37.5 mg ▼ | ☑ |

*SNRI*
TYPICAL DOSE INCREASE: 75 mg
EFFECTIVE DOES RANGE: 75 - 375 mg
MIN & MAX DOSE RANGE: 40 - 100 mg
DOSING TIPS: *START AT 37.5 mg qd* FOR ONE WEEK THEN INCREASE TO 75 mg qd.

CLINICAL PEARLS: •MAY BE HELPFUL FOR PAIN (CANMAT LEVEL 2).

*34.14% PROBABILITY OF REMISSSION, WHICH REPRESENTS A DIFFERENCE OF 3.71% COMPARED TO THE + MORE PATIENT'S MEAN PROBABILITY OF REMISSION ACROSS ALL PREDICTED TREATMENTS.*

SYSTEMS AND METHODS FOR TREATMENT SELECTION

CROSS-REFERENCE TO RELATED APPLICATIONS

This application is a continuation of International Patent Application No. PCT/CA2021/050446, filed on Apr. 1, 2021, which claims the benefit of U.S. Provisional Patent Application No. 63/004,720, filed Apr. 3, 2020, and U.S. Provisional Patent Application No. 63/079,161, filed Sep. 16, 2020, each of which is incorporated by reference herein in its entirety.

BACKGROUND

When treating a patient suffering from a medical condition, such as a mental disorder, a clinician may select from various treatment options. The available treatments may include medication. Typically, when selecting a medication to treat the patient, the clinician will attempt to classify the patient in order to select a treatment that the clinician believes will be effective. Patients are frequently treated with medication that is either not effective or is not the most effective available treatment for the patient.

SUMMARY

Patient data may be collected, such as using a questionnaire. The patient may be subject to a medical condition, such as major depressive disorder. The patient data may be input to a machine learning algorithm (MLA) that was trained to predict whether various treatments will lead the patient to remission. The MLA may output a list of treatments and the likelihood that each treatment will lead to remission. Remission is related to a success of the treatment. A clinician may review the treatments and create a treatment plan.

Prototypes may be defined that are representative of clusters of patients. The likelihood that a treatment leads to remission may be determined for each of the prototypes. The distance between the patient and each of the prototypes may be determined. The prototype closest to the patient may be output to the clinician.

The MLA may have been generated using data from studies relating to treatments for a medical condition. For example an MLA for generating results regarding major depressive disorder may be generated based on datasets from studies on treatments for major depressive disorder. Study data from each study may be retrieved. The different studies may use different questionnaires for gather data on patients in the study. The study data from each study may be normalized, such as by grouping questions in different studies that are related. A normalized dataset may be generated that includes data from multiple studies, where the different studies used different questionnaires. The normalized dataset may be used to train the MLA.

According to a first broad aspect of the present technology, there is provided a method comprising: receiving questionnaire responses from a patient requiring treatment; inputting the questionnaire responses from the questionnaire into a machine learning algorithm (MLA), wherein the MLA was trained based on labelled patient data, wherein each data point in the labelled patient data comprises questionnaire data corresponding to a respective patient and a label indicating an efficacy of a treatment for the respective patient; receiving, from the MLA, a predicted efficacy of one or more treatments for the patient; receiving, from the MLA, a prototype corresponding to the patient; generating, based on the predicted efficacy of the one or more treatments and the prototype, an interface; and outputting for display the interface.

In some implementations of the method the interface comprises, for each of the one or more treatments, a predicted likelihood of remission.

In some implementations of the method, the method further comprises receiving, via the interface, user input indicating a treatment plan, wherein the treatment plan comprises at least one of the one or more treatments.

In some implementations of the method, the method further comprises sending a request, based on the treatment plan, for obtaining medication corresponding to the treatment plan.

In some implementations of the method, the questionnaire comprises information regarding the patient's mental health.

In some implementations of the method, the questionnaire comprises information regarding the patient's medical history.

In some implementations of the method, the questionnaire comprises information regarding the patient's current medications.

In some implementations of the method, receiving the questionnaire responses comprises retrieving, from a database, the questionnaire responses.

According to another broad aspect of the present technology, there is provided a method comprising: receiving datasets from one or more sources corresponding to treatments for mental illness, wherein each data point in the datasets comprises questionnaire data corresponding to a patient and an indication of treatment efficacy corresponding to the respective patient; normalizing the results of the datasets, thereby generating normalized results; generating, based on the normalized results, a training dataset; selecting one or more features in the training dataset; and training, using the selected one or more features, a machine learning algorithm (MLA) to predict, for input patient data, an efficacy of each of the treatments.

In some implementations of the method, each dataset of the datasets comprises results of a study.

In some implementations of the method, the method further comprises training the MLA to determine a prototype corresponding to the input patient data.

In some implementations of the method, the prototype corresponds to a cluster of patient data. Each prototype may correspond to a group of patients that have similar characteristics, present similar symptoms and/or respond similarly to one or more treatments. The prototypes may be defined so that each prototype responds differently to the available treatments.

In some implementations of the method, training the MLA to determine a prototype corresponding to the input patient data comprises training the MLA based at least in part on a prototype sample distance variance.

In some implementations of the method, the method further comprises determining a prototype sample distance variance based at least in part on a variance of distances between a set of nearest samples for a given prototype and the given prototype itself.

In some implementations of the method, the method further comprises determining a prototype sample distance variance based at least in part on variance of pairwise distances between a plurality of prototypes.

In some implementations of the method, the method further comprises determining a prototype remission prediction based at least in part on variance of differential remission predictions for a plurality of prototypes across a treatment type.

In some implementations of the method, the method further comprises determining a prototype remission prediction based at least in part on variance of differential remission predictions for a given prototype across a plurality of treatment types.

In some implementations of the method, the training is performed using a loss function, and wherein the loss function determines a difference between a predicted likelihood of remission and a labeled occurrence of remission.

In some implementations of the method, the loss function determines an autoencoder loss indicating a distance between an original sample and a decoded sample.

In some implementations of the method, the loss function determines a distance between prototypes.

In some implementations of the method, the loss function determines a variance in remission predictions between the prototypes.

In some implementations of the method, normalizing the results of the datasets comprises grouping questions in different datasets relating to a same feature.

In some implementations of the method, normalizing the results of the datasets comprises converting categorical responses in the datasets to binary responses.

According to another broad aspect of the present technology, there is provided a system comprising: at least one processor, and memory storing a plurality of executable instructions which, when executed by the at least one processor, cause the system to: receive questionnaire responses from a patient requiring treatment; input the questionnaire responses from the questionnaire into a machine learning algorithm (MLA), wherein the MLA was trained based on labelled patient data, wherein each data point in the labelled patient data comprises questionnaire data corresponding to the respective patient and a label indicating an efficacy of a treatment for the respective patient; receive, from the MLA, a predicted efficacy of one or more treatments for the patient; receive, from the MLA, a prototype corresponding to the patient; generate, based on the predicted efficacy of the one or more treatments and the prototype, an interface; and output for display the interface.

In some implementations of the system, the system further comprises a display, and the instructions that cause the system to output for display the interface comprise instructions that cause the system to output, by the display, the interface.

According to another broad aspect of the present technology, there is provided a system comprising: at least one processor, and memory storing a plurality of executable instructions which, when executed by the at least one processor, cause the system to: receive datasets from one or more sources corresponding to treatments for mental illness, wherein each data point in the datasets comprises questionnaire data corresponding to a patient in and an indication of treatment efficacy corresponding to the respective patient; normalize the results of the datasets, thereby generating normalized results; generate, based on the normalized results, a training dataset; select one or more features in the training dataset; and train, using the selected one or more features, a machine learning algorithm (MLA) to predict, for input patient data, an efficacy of each of the treatments. Various implementations of the present technology provide a non-transitory computer-readable medium storing program instructions for executing one or more methods described herein, the program instructions being executable by a processor of a computer-based system.

Various implementations of the present technology provide a computer-based system, such as, for example, but without being limitative, an electronic device comprising at least one processor and a memory storing program instructions for executing one or more methods described herein, the program instructions being executable by the at least one processor of the electronic device.

It should be expressly understood that not all technical effects mentioned herein need be enjoyed in each and every embodiment of the present technology.

As used herein, the wording "and/or" is intended to represent an inclusive-or; for example, "X and/or Y" is intended to mean X or Y or both. As a further example, "X, Y, and/or Z" is intended to mean X or Y or Z or any combination thereof.

In the context of the present specification, unless expressly provided otherwise, a computer system or computing environment may refer, but is not limited to, an "electronic device," a "computing device," an "operation system," a "system," a "computer-based system," a "computer system," a "network system," a "network device," a "controller unit," a "monitoring device," a "control device," a "server," and/or any combination thereof appropriate to the relevant task at hand.

In the context of the present specification, unless expressly provided otherwise, any of the methods and/or systems described herein may be implemented in a cloud-based environment, such as, but not limited to, a Microsoft Azure environment, an Amazon EC2 environment, and/or a Google Cloud environment.

In the context of the present specification, unless expressly provided otherwise, the expression "computer-readable medium" and "memory" are intended to include media of any nature and kind whatsoever, non-limiting examples of which include RAM, ROM, disks (e.g., CD-ROMs, DVDs, floppy disks, hard disk drives, etc.), USB keys, flash memory cards, solid state-drives, and tape drives. Still in the context of the present specification, "a" computer-readable medium and "the" computer-readable medium should not be construed as being the same computer-readable medium. To the contrary, and whenever appropriate, "a" computer-readable medium and "the" computer-readable medium may also be construed as a first computer-readable medium and a second computer-readable medium.

In the context of the present specification, unless expressly provided otherwise, the words "first," "second," "third," etc. have been used as adjectives only for the purpose of allowing for distinction between the nouns that they modify from one another, and not for the purpose of describing any particular relationship between those nouns.

Additional and/or alternative features, aspects and advantages of implementations of the present technology will become apparent from the following description, the accompanying drawings, and the appended claims.

BRIEF DESCRIPTION OF THE DRAWINGS

For a better understanding of the present technology, as well as other aspects and further features thereof, reference is made to the following description which is to be used in conjunction with the accompanying drawings, where:

FIG. 5 illustrates an exemplary interface with patient prototypes in accordance with various embodiments of the present technology;

FIG. 8 illustrates an exemplary interface for selecting treatments in accordance with various embodiments of the present technology; and FIG. 9 illustrates an exemplary interface for adjusting treatments in accordance with various embodiments of the present technology.

DETAILED DESCRIPTION

Figure 1:
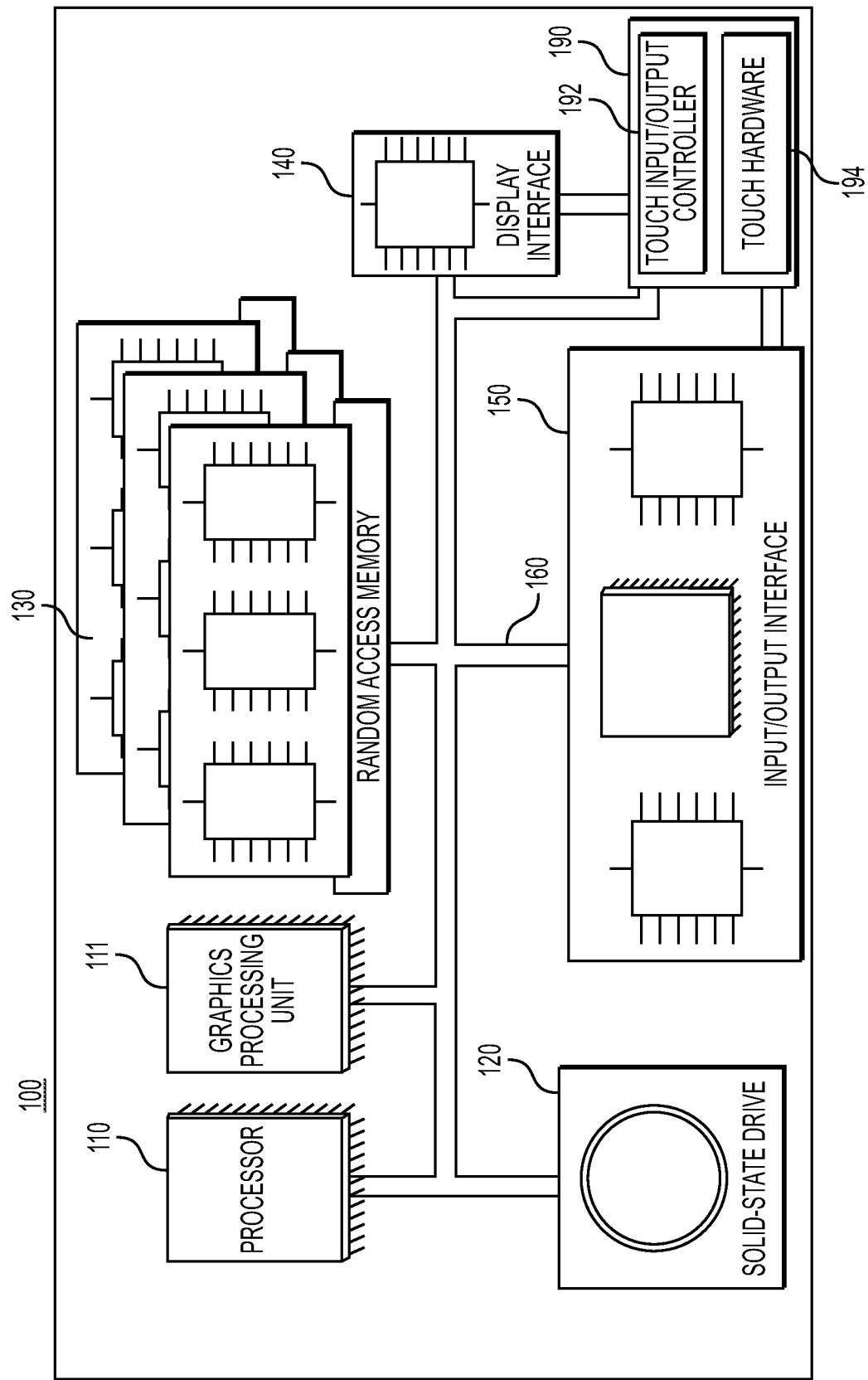
FIG. 1 is a block diagram of an example computing environment in accordance with various embodiments of the present technology.

The examples and conditional language recited herein are principally intended to aid the reader in understanding the principles of the present technology and not to limit its scope to such specifically recited examples and conditions. It will be appreciated that those skilled in the art may devise various arrangements which, although not explicitly described or shown herein, nonetheless embody the principles of the present technology and are included within its spirit and scope.

Furthermore, as an aid to understanding, the following description may describe relatively simplified implementations of the present technology. As persons skilled in the art would understand, various implementations of the present technology may be of greater complexity.

In some cases, what are believed to be helpful examples of modifications to the present technology may also be set forth. This is done merely as an aid to understanding, and, again, not to define the scope or set forth the bounds of the present technology. These modifications are not an exhaustive list, and a person skilled in the art may make other modifications while nonetheless remaining within the scope of the present technology. Further, where no examples of modifications have been set forth, it should not be interpreted that no modifications are possible and/or that what is described is the sole manner of implementing that element of the present technology.

Moreover, all statements herein reciting principles, aspects, and implementations of the present technology, as well as specific examples thereof, are intended to encompass both structural and functional equivalents thereof, whether they are currently known or developed in the future. Thus, for example, it will be appreciated by those skilled in the art that any block diagrams herein represent conceptual views of illustrative circuitry embodying the principles of the present technology. Similarly, it will be appreciated that any flowcharts, flow diagrams, state transition diagrams, pseudocode, and the like represent various processes which may be substantially represented in computer-readable media and so executed by a computer or processor, whether or not such computer or processor is explicitly shown.

The functions of the various elements shown in the figures, including any functional block labeled as a "processor," may be provided through the use of dedicated hardware as well as hardware capable of executing software in association with appropriate software. When provided by a processor, the functions may be provided by a single dedicated processor, by a single shared processor, or by a plurality of individual processors, some of which may be shared. In some embodiments of the present technology, the processor may be a general purpose processor, such as a central processing unit (CPU) or a processor dedicated to a specific purpose, such as a digital signal processor (DSP). Moreover, explicit use of the term a "processor" should not be construed to refer exclusively to hardware capable of executing software, and may implicitly include, without limitation, application specific integrated circuit (ASIC), field programmable gate array (FPGA), read-only memory (ROM) for storing software, random access memory (RAM), and non-volatile storage. Other hardware, conventional and/or custom, may also be included.

Software modules, or simply modules which are implied to be software, may be represented herein as any combination of flowchart elements or other elements indicating performance of process steps and/or textual description. Such modules may be executed by hardware that is expressly or implicitly shown. Moreover, it should be understood that one or more modules may include for example, but without being limitative, computer program logic, computer program instructions, software, stack, firmware, hardware circuitry, or a combination thereof.

Computing Environment

FIG. 1 illustrates a computing environment 100, which may be used to implement and/or execute any of the methods described herein. In some embodiments, the computing environment 100 may be implemented by any of a conventional personal computer, a computer dedicated to managing network resources, a network device and/or an electronic device (such as, but not limited to, a mobile device, a tablet device, a server, a controller unit, a control device, etc.), and/or any combination thereof appropriate to the relevant task at hand. In some embodiments, the computing environment 100 comprises various hardware components including one or more single or multi-core processors collectively represented by processor 110, a solid-state drive 120, a random access memory 130, and an input/output interface 150. The computing environment 100 may be a computer specifically designed to operate a machine learning algorithm (MLA). The computing environment 100 may be a generic computer system.

In some embodiments, the computing environment 100 may also be a subsystem of one of the above-listed systems. In some other embodiments, the computing environment 100 may be an "off-the-shelf" generic computer system. In some embodiments, the computing environment 100 may also be distributed amongst multiple systems. The computing environment 100 may also be specifically dedicated to the implementation of the present technology. As a person in the art of the present technology may appreciate, multiple variations as to how the computing environment 100 is implemented may be envisioned without departing from the scope of the present technology.

Those skilled in the art will appreciate that processor 110 is generally representative of a processing capability. In some embodiments, in place of or in addition to one or more conventional Central Processing Units (CPUs), one or more specialized processing cores may be provided. For example, one or more Graphic Processing Units (GPUs), Tensor Processing Units (TPUs), and/or other so-called accelerated processors (or processing accelerators) may be provided in addition to or in place of one or more CPUs.

System memory will typically include random access memory 130, but is more generally intended to encompass any type of non-transitory system memory such as static random access memory (SRAM), dynamic random access memory (DRAM), synchronous DRAM (SDRAM), read-only memory (ROM), or a combination thereof. Solid-state drive 120 is shown as an example of a mass storage device, but more generally such mass storage may comprise any type of non-transitory storage device configured to store data, programs, and other information, and to make the data, programs, and other information accessible via a system bus 160. For example, mass storage may comprise one or more of a solid state drive, hard disk drive, a magnetic disk drive, and/or an optical disk drive.

Communication between the various components of the computing environment 100 may be enabled by a system bus 160 comprising one or more internal and/or external buses (e.g., a PCI bus, universal serial bus, IEEE 1394 "Firewire" bus, SCSI bus, Serial-ATA bus, ARINC bus, etc.), to which the various hardware components are electronically coupled.

The input/output interface 150 may allow enabling networking capabilities such as wired or wireless access. As an example, the input/output interface 150 may comprise a networking interface such as, but not limited to, a network port, a network socket, a network interface controller and the like. Multiple examples of how the networking interface may be implemented will become apparent to the person skilled in the art of the present technology. For example the networking interface may implement specific physical layer and data link layer standards such as Ethernet, Fibre Channel, Wi-Fi, Token Ring or Serial communication protocols. The specific physical layer and the data link layer may provide a base for a full network protocol stack, allowing communication among small groups of computers on the same local area network (LAN) and large-scale network communications through routable protocols, such as Internet Protocol (IP).

The input/output interface 150 may be coupled to a touchscreen 190 and/or to the one or more internal and/or external buses 160. The touchscreen 190 may be part of the display. In some embodiments, the touchscreen 190 is the display. The touchscreen 190 may equally be referred to as a screen 190. In the embodiments illustrated in FIG. 1, the touchscreen 190 comprises touch hardware 194 (e.g., pressure-sensitive cells embedded in a layer of a display allowing detection of a physical interaction between a user and the display) and a touch input/output controller 192 allowing communication with the display interface 140 and/or the one or more internal and/or external buses 160. In some embodiments, the input/output interface 150 may be connected to a keyboard (not shown), a mouse (not shown) or a trackpad (not shown) allowing the user to interact with the computing device 100 in addition to or instead of the touchscreen 190.

According to some implementations of the present technology, the solid-state drive 120 stores program instructions suitable for being loaded into the random access memory 130 and executed by the processor 110 for executing acts of one or more methods described herein. For example, at least some of the program instructions may be part of a library or an application.

Treatment Selection System

Figure 2:
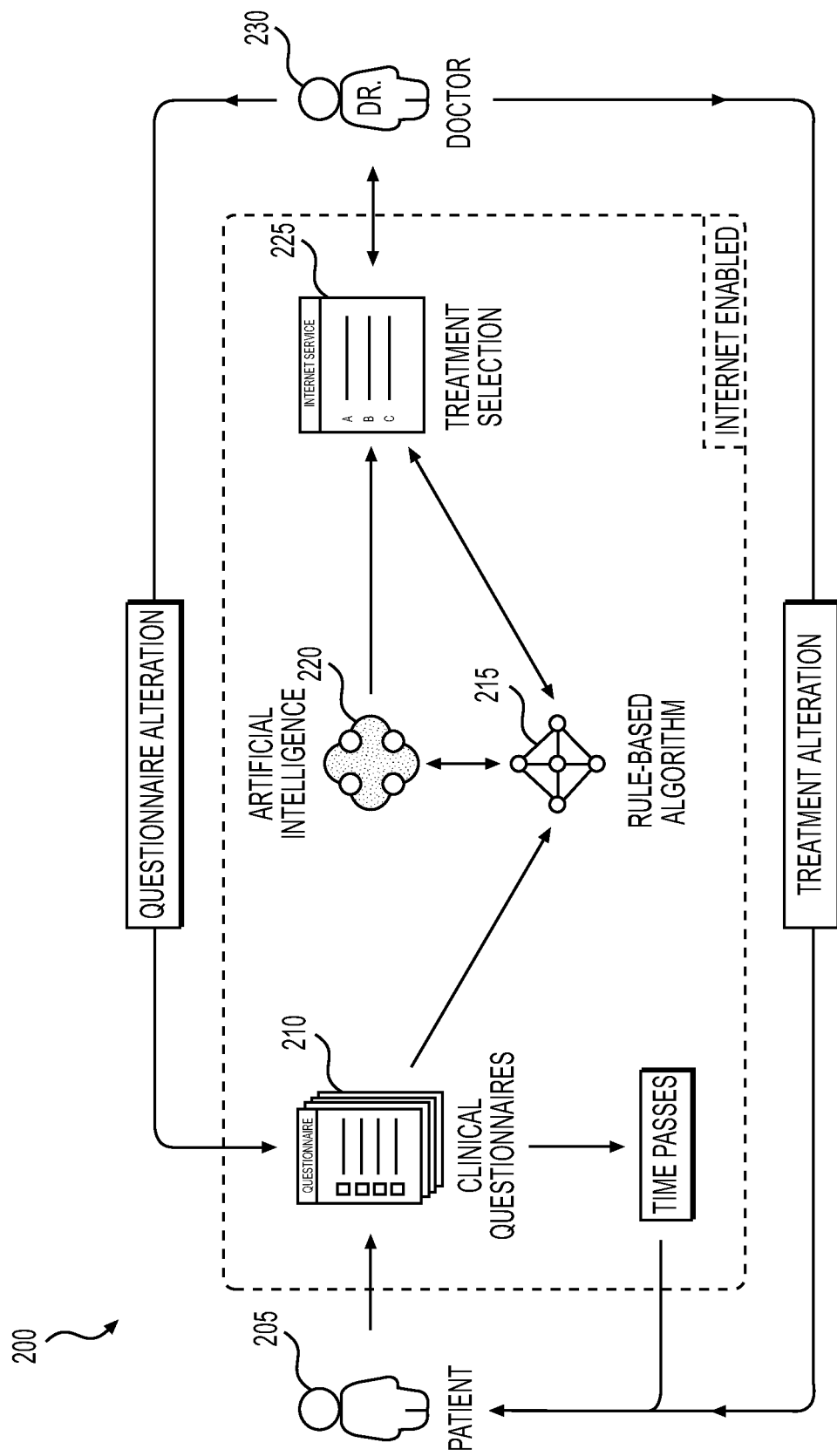
FIG. 2 is a diagram of a system for treatment selection in accordance with various embodiments of the present technology.

FIG. 2 is a diagram of a system 200 for treatment selection in accordance with various embodiments of the present technology. The system 200 may be used for generating results and information that can assist a doctor 230 in treatment selection for a patient 205. The patient 205 may be subject to a medical condition such as major depressive disorder. The patient 205 may complete a clinical questionnaire 210. The clinical questionnaire may include questions relating to the patient's 205 mental health, medical history, family medical history, current medications, and/or any other type of questions. The patient 205 may be periodically asked to update the clinical questionnaire 210 and/or complete a new clinical questionnaire 210, so that the information collected regarding the patient 205 is up-to-date. The patient 205 may be asked to update the clinical questionnaire 210 after a pre-determined amount of time has passed. The clinical questionnaire 210 may be completed by the patient 205, a caregiver of the patient 205, and/or the doctor 230.

The results of the clinical questionnaire 210 may be transmitted to a rule-based algorithm 215 and/or an artificial intelligence system 220. The rule-based algorithm 215 may be a clinical rule-based algorithm based on existing treatment guidelines, such as existing guidelines for the treatment of major depressive disorder. The rule-based algorithm 215 and/or artificial intelligence system 220 may be implemented on a server, such as in a cloud platform. The rule-based algorithm 215 and/or artificial intelligence system 220 may predict the efficacy of one or more treatments for the patient 205 based on the responses to the clinical questionnaire 210. The efficacy of the one or more treatments may be assessed in various different ways and/or may be specific to a medical condition. The efficacy may be determined based on a likelihood that treatment leads to remission, an amount of time to remission, whether the treatment is likely to cause harm and/or have harmful side effects, whether treatment will resolve certain symptoms, whether treatment will lead to a return to a base line physiological measurement, and/or any other measure of a treatment's efficacy.

The artificial intelligence system 220 may be trained to predict the likelihood of remission for a patient if the patient is given various treatments. For each potential treatment, the artificial intelligence system 220 may output a predicted likelihood of remission. The rule-based algorithm 215 and/or artificial intelligence system 220 may output a treatment selection interface 225. The artificial intelligence system 220 may include one or more MLAs, such as an MLA generated using the method 300, described in further detail below.

A patient may be considered to be in remission when there is an absence and/or relatively low level of symptoms present. The method of determining whether a patient is in remission may be specific to each different medical condition. Remission may be defined in relation to the threshold for remission on a validated standardized questionnaire. For example a patient may be determined to be in remission for depression based on the Hamilton Depression Rating Scale (HAM-D), Montgomery-Asberg Depression Rating Scale (MADRS), The Inventory of Depressive Symptomatology (IDSC), or The 16-item Quick Inventory of Depressive Symptomatology (QIDS-SR-16), and/or any other questionnaire.

The predicted likelihood of remission for each treatment may be displayed on the treatment selection interface 225. The treatment selection interface 225 may be output for display to a system used by a doctor 230, such as a desktop computer or mobile device used by the doctor 230. The doctor 230 may review the treatment selection interface 225. The treatment selection interface 225 may provide information that assists the doctor 230 in treatment selection. The doctor 230 may interact with the treatment selection interface 225. The doctor 230 may select a treatment for the patient 205 and input the treatment to the treatment selection interface 225.

The doctor 205 may input, via the treatment selection interface 225, the selected treatment, dosage amount, notes, and/or any other information regarding treatment for the patient 205. The doctor 230 may input answers and/or alterations to the clinical questionnaire 210. For example the doctor may alter the responses to the clinical questionnaire 210 that were input by the patient 205, such as based on conversations between the doctor 230 and patient 205. The updated data may then be used to generate an updated treatment selection interface 225 based on the input received from the doctor 230.

Training an MLA

Figure 3:
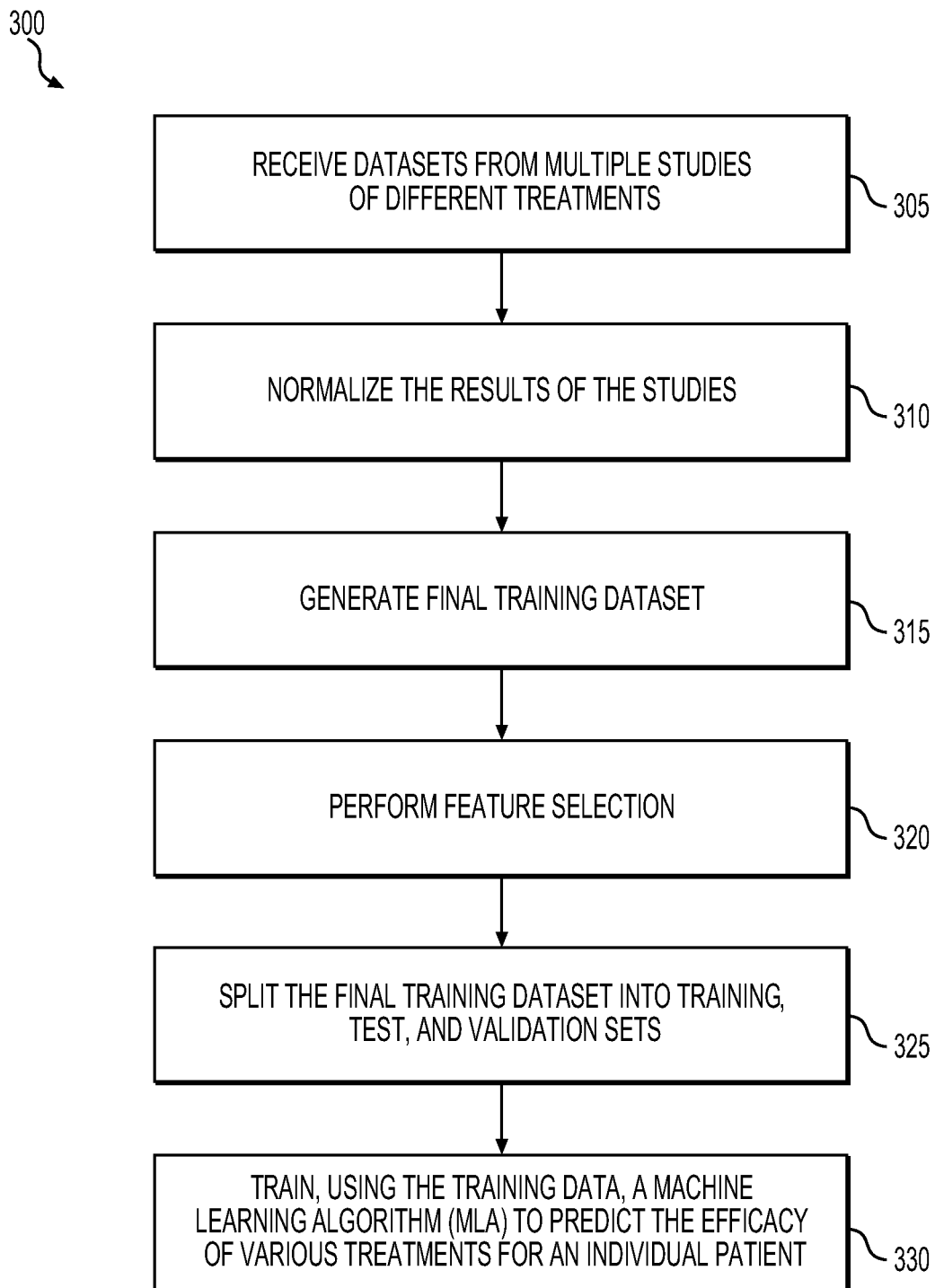
FIG. 3 illustrates a flow diagram of a method for training a machine learning algorithm (MLA) for predicting treatment efficacy in accordance with various embodiments of the present technology.

FIG. 3 illustrates a flow diagram of a method 300 for training a machine learning algorithm (MLA) for predicting treatment efficacy in accordance with various embodiments of the present technology. In one or more aspects, the method 300 or one or more steps thereof may be performed by a computing system, such as the computing environment 100. The method 300 or one or more steps thereof may be embodied in computer-executable instructions that are stored in a computer-readable medium, such as a non-transitory mass storage device, loaded into memory and executed by a CPU. Some steps or portions of steps in the flow diagram may be omitted or changed in order At step 305 datasets may be received from multiple studies. Each dataset may include multiple data points, where each data point corresponds to a single patient. The studies may test the efficacy of one or more treatments for a medical condition, such as major depressive disorder. The datasets may be in a table format and/or any other suitable format. The datasets may be retrieved from and/or stored in a database. Each dataset of study data may include clinical data, demographic data, outcome data and/or any other data from the study. The datasets may consist of individual patient level data from previous studies of patients being treated for a medical condition, such as major depressive disorder. Each dataset may correspond to a single study.

The datasets may be filtered to remove any placebo data in the datasets. After filtering, the datasets may solely contain data from active groups in the studies. In some instances placebo data may be retained either in the datasets or in a separate dataset, such as for performing a comparison to placebo data.

The datasets may be generated from various different types of studies. Datasets may have been generated from double blinded placebo controlled trials, open-label studies, and/or any other type of study. Information regarding the type of study that was used to generate a dataset may be stored in the dataset and/or otherwise associated with the dataset. In order to reduce and/or eliminate the influence of study type on predictions, variables representing the study type may be examined to determine if and/or how they influence predictions.

At step 310 the results of the studies may be normalized and/or combined. The results may be normalized using standard statistical processes (i.e. based on standard deviation) and/or by matching of similar features in each study. Step 310 may be performed if the studies used different questionnaires measuring similar constructs. By normalizing the data, results may be compared between different studies that used different questionnaires. For example, two studies may use two different questions that both ask about insomnia at the start of the night. These questions, if they are assessing the same construct (i.e. early insomnia in this case) can be matched and then combined via a normalization process.

Questions associated with a same known construct may be identified and grouped together. The questions may originate from different studies and/or different questionnaires. As an example, the following questions from different studies may be grouped into the category of "anhedonia" based on the question text: "loss of pleasure in all, or almost all, activities," "less pleasure from things," "I have lost all pleasure in life," "markedly diminished interest or pleasure in all, or almost all, activities most of the day, nearly every day." While these questions are not identical, they each may probe the same symptom dimension, which in this case is anhedonia. If the answer to the questions are not in a binary format, such as if they are categorical responses, the responses may be converted into a binary format (i.e. "yes" and "no"). The responses may be converted to a binary format so that the resolution of the information is consistent across questionnaires. In this manner, disparate datasets can be combined to prevent sparse data storage which may make downstream modelling less efficient and/or less effective.

A common data frame may be created and equivalent questions may be grouped according to various constructs (i.e. mood or sleep symptom clusters). In order to group equivalent questions, pairs of questions (e.g. being a part of a different questionnaire and not being a part of the same one) may be semantically grouped so that instead of being tracked independently, which may introduce more noise to the ability of a downstream algorithm to identify hidden patterns, they can be combined so that the same information is coupled together across studies.

At step 315 training data may be generated based on the normalized study results. The amalgamated data generated at step 310, which may include all or a portion of the datasets received at step 305, may be used to generate a final training dataset. Each data point in the final training dataset may include answers to various questions for a patient and a label for the patient. The label may indicate whether the treatment led to remission.

At step 320 a feature selection process may be performed. Each data point in the final training dataset may include various features. A subset of the features may be selected for training the MLA. A feature selection process may be applied to the final training dataset generated at 315 to determine which features will be used. Any feature selection algorithm may be used. The feature selection algorithm may output one or more features of the final training dataset.

The features may be selected based on the determined influence of the features on the results of the final predictive objective. For example, in order to predict treatment efficacy, the MLA may be trained to determine if a certain prescribed treatment will lead to remission for any given patient. Features may be selected that appear to influence whether the prescribed treatment will lead to remission.

Features may be selected based on intrinsic patterns that exist in the training data. The MLA's ability to associate a treatment efficacy to a patient may be affected by which features are selected. If the features selected at step 320 are not sufficiently information rich, the performance of the MLA may deteriorate. Features may be selected that align patterns found in the data with their ability to determine if a treatment will lead a patient to remission. Features having a highest amount of influence may be selected at step 320.

If the features that are selected do not result in an MLA that is considered suitable for predicting whether a treatment will lead a patient to remission, features may be added and/or removed from the set of features used to train the MLA. A portion of the dataset may be reserved for testing and/or validation of the MLA. The suitability of the MLA may be determined based on how accurate the MLA is in predicting whether a treatment will lead a patient to remission. Examples of features that may be contained in the datasets and/or selected are included in Table 1 below. It should be understood that the features listed in Table 1 are exemplary, and that other features may be contained in the datasets and/or generated using the datasets.

TABLE 1

| Examples of features | | | |
|---|---|---|---|
| Abuse | Eating disorder | Mobility | Race |
| Addiction symptoms | ECG | Mood | Reactivity |
| ADHD | ECT | Mother treated violently | Recent life stress |
| ADHD symptoms | Educational attainment | Motivation | Reckless overconfidence |
| Adherence | Emotional | Muscular | Recurrent episodes |
| Adjustment disorders | Employment status | Narcissistic | Related to guilt |
| Adopted | Enclosure | Negative symptoms | Relationships |
| Adverse effects | Energy | Neglect | Residence |
| Age | Engagement/ interest | Neuro-developmental and related disorders | Respiratory |
| Age first received psychiatric treatment | Ethnicity | Neurological | Respiratory rate |
| Age of MDD onset | Euphoric activation | Neuromodulation | Restrictive eating |
| Age of onset | Excoriation disorder | Neuroticism | Romantic |
| Agoraphobia | Executive Function | Non-biological family | rTMS |
| Agoraphobic | Exercise | Number of acts | Rumination |
| Alcohol | Family | Number of children | Rural/urban |
| Anger | Family history | Number of cigarettes per day | Sadness |
| Anhedonia | Fear | Number of cigars per day | Satisfaction with medication |
| Anorexia nervosa | Frequency | Number of cups per day | Schizoaffective disorder |
| Antisocial | Functional impairment | Number of drinks per week | Schizoid |
| Anxiety | Future | Number of episodes | Schizophrenia |
| Anxiety symptoms | Gambling | Number of hospitalizations | Schizotypal |
| Appetite | Gastrointestinal | Number of pipes per day | School/work |
| Auditory | Gender | Number of previous attempts | Seasonal-related |
| Autism spectrum | Gender dysphoria | Number of previous episodes | Self care |
| Autonomic | Generalized anxiety disorder | Numbing | Self-appraisal |
| Avoidance | Genes | Obsession | Self-harm |
| Avoidant | Genito-urinary | Obsessive compulsive | Self-referential thinking |
| Avoidant restrictive food intake disorder | Grandiose | Obsessive compulsive and related disorder | Self-worth |
| Being punished | Guilt | Obsessive compulsive and related disorders | Sensation of heaviness in limbs or back or head |
| Binge eating disorder | Hallucination | Obsessive compulsive symptoms | Sensitivity |
| Binging | Hallucinations | OCD | Sensory |
| Biofluids | Handedness | Olfactory/ Tactile/ Gustatory | Severity |
| Biological family | Head circumference | Oppositional defiant disorder | Severity/ tolerability |
| Bipolar disorder | Headache | Optimism/ Pessimism | Sex |
| Blood pressure | Health-related | Orphanage/ foster care experience | Sexual |
| BMI | Heart rate | OSFED | Sleep |
| Body dysmorphia | Heart rate variability | Other | Smoking status |
| Body fat percentage | Height | Other caffeinated beverages | Social |
| Body Temperature | Hip circumference | Other major affective disturbance | Socio-demographic |
| Borderline | Histrionic | Other psychotic disturbance | Socioeconomic status |
| Boredom | Hopelessness | other specified ADHD | Somatic |
| Bulimia nervosa | Hormone replacement therapy | Other specified obsessive compulsive and related disorder | Specific phobia |
| Bullying | Hospitalization | Other specified tic disorder | Standard |
| Caffeine consumption | Hospitalization specifically for suicide | Outlook | States and Traits |
| Cardiac | Hospitalized for any psychiatric disturbance | Outpatient | Stress disorders |
| Children Chromosomal abnormality | Hostility Household activities | Overwhelm Pain | Stress/trauma Substance abuse |
| Classes | Household dysfunction | Panic attacks | Substance abuse-alcohol |
| Clinician-patient relationship | Hyperactive cognition | Panic disorder | Substance abuse-drugs |
| Cluster A | Hyperarousal | Paranoia | Substance use |
| Cluster B | Hypersomnia | Paranoid | Substance use disorder |
| Cluster C | Hypomania | Parents | Substance-related |
| Coffee drinking | Immigrant status | Partial hospitalization | Suicidal ideation |
| Cognitive | Impulsivity | Paternal | Suicidality |
| Cognitive symptoms | Incarcerated relative | Persistent/ chronictic disorder | Suicide |
| Combined presentation | Incarceration | Personal | Suicide attempts |
| Concentration | Increased appetite | Personal history | Symmetry/ ordering/ arranging |
| Condition | Inpatient | Personality disorder | Systolic |
| Confusion | Insight | Pervasive developmental disorder | tDCS |

TABLE 1-continued

Examples of features

| | | | |
|---|---|---|---|
| Contamination/ cleaning | Insomnia | Pharmacology | Tension |
| Contraception | Intellectual disability | Phobia | Thoughts and beliefs |
| Country of origin | Intensity | Physical | Tic disorder |
| Crying | Interpersonal | Physical activity | Tic symptoms |
| CYP1A2 | Interval between remission of last episode to start of current episode | Physiology | Time since first episode of MDD |
| CYP2B6 | Intrusions | Planning | Tourette's syndrome |
| CYP2C19 | IQ | Positive symptoms | Traumatic brain injury |
| CYP2D6 | Irritability | Post traumatic stress | Treatment |
| CYP3A4POR | Laboratory values | Post-childhood trauma | Trembling/ shaking |
| Decision making | Lassitude | predominantly hyperactive/ impulsive presentation | Trichotillomania |
| Decreased appetite | Late | predominantly inattentive presentation | Trichotillomania symptoms |
| Delusion | Legal | Pregnancy | Trouble relaxing |
| Delusional disorder | Leisure | Pregnancy-related | Type 1 |
| Delusions | Level of social support | Premenstrual dysphoric disorder | Type 2 |
| Dependent | Life satisfaction | Preparatory acts | Type of care |
| Depression | Living arrangement | Previous episodes | Type/ arrangement |
| Depression secondary to another cause | Loneliness | Primary language spoken | Unspecified ADHD |
| Diastolic | Major depressive disorder | Provisional tic disorder | Unspecified eating disorder |
| Disordered eating symptoms | Mania | Psychiatric | Unspecified obsessive compulsive and related disorder |
| Disorganization | Manic episodes | Psychiatric medication | Unspecified tic disorder |
| Dissociation | Marital status | Psychic | Variation |
| Diurnal | Maternal | Psychomotor agitation | Violence |
| Divorce | Medical | Psychomotor arousal | Violent/sexual/ religious content |
| Dizziness/ Lightheadedness | Medication response | Psychomotor retardation | Visual |
| Doubting/ checking | Memory | Psychotherapy | Vomiting |
| Drugs | Menopausal status | Psychotic disorders | Waist circumference |
| Due to another medical condition | Menstrual-related | Psychotic symptoms | Waist/hip ratio |
| Duration | Menstruation | PTSD | Weight |
| Duration of last episode | Mental deficiency | Public | Weight gain |
| Duration of living at current residence | Mental illness | Purging | Weight loss |
| Dysthymia | Metabolizer status i.e. normal or poor or rapid | Quality of life | Working memory |
| Early Early life stress | Method Middle | Quality of mood Quitting status | Worry Years of smoking Years since immigration |

This table presents a list of features in a tabulated format.

At step 325 the final training dataset may be split into training, test, and/or validation sets. Each data point in the final training dataset may be assigned to either the training, test, or validation set. Any technique may be used for separating the dataset into the training, test, and/or validation sets, such as randomly selecting data points in the final training dataset for each of the sets. The training, test, and/or validation sets may be assigned a predetermined amount or proportion of data points. For example the training set may include 60% of the data points in the final training dataset, the test set may include 20% of the data points in the final training dataset, and the validation set may include 20% of the data points in the final training dataset. Other rules are possible.

At step 330 the MLA may be trained with the objective of accurately predicting remission rates for each treatment. The MLA may receive the training set of data points from the final training dataset. For each data point received, the MLA may predict, based on the features, a likelihood that the treatment will lead the patient to remission. The predicted likelihood may be compared to the label for the data point, which indicates whether or not the treatment led to remission. A loss function, described in further detail below, may be used to compare the label to the MLA output. The MLA may be adjusted based on a difference between the predicted likelihood and the label. In this manner, the MLA may be trained to receive a data point including the features selected at step 320 and output a predicted likelihood that the treatment will lead the patient to remission.

The MLA Architecture

The MLA may comprise one or more neural networks and/or any other type of machine-learning model. The MLA may be referred to as a DifferentialPrototypeNet. The MLA may be composed of a symmetrical auto-encoder whose input, x, lacks the treatment assigned to the patient and is responsible for encoding features corresponding to the patient into some latent space, e(x). A decoder may decode back the encoded features to the original input, d(e(x)). The decoded features might not be identical to the original features that were encoded.

As discussed above, a clinical questionnaire 210 may be administered to a patient. The questionnaire may include questions involving features listed in Table 1 above. Answers to the questions may be encoded into a vector of numbers using an encoder function e(x). The vector may then be input to the MLA.

Prototypes

Various prototypes may be defined corresponding to clusters of patients. Each prototype may correspond to a group of patients that have similar characteristics, present similar symptoms and/or respond similarly to one or more treatments. The prototypes may be defined so that each prototype responds differently to the available treatments. The prototypes may assist the clinician and/or patient in understanding the results that are output by the MLA. In other words, the prototypes may be used to enhance the interpretability of the results for the clinician and/or patient. Each prototype may be used to generate an exemplary patient corresponding to the prototype in order to compare a real patient to this prototype.

The training of the MLA may involve a layer of a neural network forming the MLA that extracts these prototypes. Each prototype may indicate the importance of features in predicting remission for patients and/or the differential effect of different treatments on a given prototype. Each prototype may be associated with a patient cluster, meaning the group of patients that are relatively similar to the learned prototypes. The prototype extraction may improve the accuracy of the MLA and/or to improve the interpretability of the MLA. The prototype extraction may assist clinicians in understanding outputs of the MLA by demonstrating how different feature clusters, representing different patient prototypes, might respond to different treatments.

The number of prototypes to be defined may be determined empirically (with human/non-human initialization and experiment progression) and/or dynamically (through algorithmic determinism to optimize a downstream objective). The number of prototypes may be selected based on various considerations, such as increasing interpretability and/or accuracy of the prototypes. For example, the number of prototypes may be set to three, which may provide a balance between providing enough nuance between the prototypes while also providing a sufficiently accurate MLA.

In some instances, the prototypes may be defined in the original feature space without use of the auto-encoder but then encoded, by the auto-encoder, into the latent space for compatibility in the comparison with already encoded features. The prototypes may be defined manually by an operator and/or automatically using various functions, such as clustering algorithms. For example an operator may input various parameters for a prototype.

Given the symmetrical nature of the neural network, the encoder and decoder may both include the same number of fully-connected layers. The encoding layer's, e(x), output may be fed into a prototype layer, p, which may be configured with k-nodes to represent each prototype separately. The variable k may represent the number of patient archetypes that the prototypes may, separately, learn to represent. Each node may be the size of the incoming data samples. The prototypes may be defined in the latent (encoded) space.

In order for a patient's data to be compared to the set of prototypes, they both can be mapped to the encoded space. The prototypes may have learned parameters which can be configured to shift around the encoded feature space in order to achieve optimal down-stream predictive performance of the MLA. The prototypes may be assigned "frozen" weights which may ensure that the prototypes remain static throughout the duration of the MLA training.

In order to render the prototypes interpretable by an operator, such as a clinician, the prototypes may be decoded by the decoder, d(p). The decoder may extract the original feature values corresponding to a prototype. A content expert, such as a clinician, may review the original feature values for prototypes to better understand the prototypes and their relationship with predicted treatment effectiveness probabilities.

When a patient's data is input to the MLA, the auto-encoder may be used in order to calculate the distance between the patient and each of the prototypes in latent space. These distances may then be passed down for downstream predictive objectives.

Prototype Configuration

Various hyperparameters may be configured when defining the prototypes, including (1) the number of prototypes that the MLA will support and (2) the tunable parameters for each prototype.

Any number of prototypes may be defined. For the purpose of improving interpretability, it may be preferable to have a relatively smaller number of prototypes, such as two, three, or four prototypes because having too many prototypes may make it difficult for a clinician to understand and/or explain why a patient might benefit from one treatment over another. From a performance perspective, the number of prototypes may also be configured to optimize a downstream objective such as predicting a remission rate for a treatment. An operator may select the number of prototypes to define in order to balance interpretability and the overall performance of the MLA.

The parameters for a prototype can be defined in various ways, such as based on input from an operator and/or automatically using functions. An operator may define parameters for a prototype. The operator may define parameters for each of the features selected at step 320. A prototype may then be generated based on the parameters defined by the operator. The parameters for a prototype may be generated using functions, such as clustering algorithms.

Previously identified stereotypical patient clusters may be used as the basis for prototypes. An operator may define parameters corresponding to the previously identified clusters, and the previously identified clusters may be translated into prototypes by passing those parameter values through the encoder e(x) in order to initialize the prototypes.

Algorithmic initialization may be used to generate the prototypes. Prototypes may be initialized using the Xavier-Glorot uniform/normal, He (i.e. Kaiming) uniform/normal, or a normal or uniform, or other pre-existing or custom distribution that allows the sampling of a set of parameters from a continuous or discrete set of values.

Prototype Output

The output of the prototype layer may represent the distance between a patient's encoded data, e(x), and each of the prototypes, p. In other words, the output may indicate a distance between the patient and each of the prototypes. This distance may be defined by the Frobenius norm between the encoded sample and each of the prototypes, separately. Any other suitable distance measure may be used, such as variance-based distance (under the assumption that each prototype represents a statistically different distribution of samples), Mahalanobis distance, or modelling each of the prototype clusters to a normal distribution to identify which patient samples are most likely to belong within some standard deviation of the cluster centers. For example, if a sample is more likely to be within one standard deviation of a first cluster than the third standard deviation of a second cluster, the distances may reflect that degree of overlap.

The patient-to-prototype latent distances may be fed into a fully connected neural layer that gets concatenated with the assigned treatment that was omitted before passing in patient information to the encoder. The treatments may be encoded in a one-hot fashion before being concatenated to the rest of the distance vector. This concatenation may feed into the final classification layers whose objective is to extract the likelihood of remission for each of the assigned treatments to test the hypothetical cases for each of the patients. These predicted remission rates for each treatment for each of the patients may then be aggregated and used to calculate the differential benefit.

Configuring the Loss Objective

At step 330 the MLA may be trained to predict the efficacy of various treatments for a patient, which may be output as the likelihood of remission with each treatment. A loss function may be used to train the MLA. For each labeled data point input to the MLA during training, the loss function may calculate a difference between the prediction and the label. The calculated loss may then be used to adjust the MLA. The MLA loss function may be composed of various subsections that act as regularizers and controls for the intended behaviour of the MLA.

The global loss which may be used to train the overall MLA may be a weighted summation of some or all of the following components:

(1) The remission classification on whether or not the likelihood of remission for a given treatment matches the true occurrence (target) for that patient. This may be characterized as a cross-entropy loss function.

(2) The autoencoder loss may be defined by the Euclidean distance between the original sample, x, and the decoded sample, d(e(x)). Other distance metrics may be used, such as, but not limited to, changes in the entropy between the distributions and Wasserstein distance.

(3) Controlling for the prototype-sample distance variance. The variance of the distance between prototypes and samples can be composed up of both (I) the (intra) variance of the distances between the nearest samples for a given prototype and the prototype itself and/or (II) the (inter) variance of the pairwise distances between all of the prototypes. These two components may be linearly combined with coefficients that can modulate their impact on the global objective. This may control the prototypes with the objective being that the prototypes are sufficiently spread out across the latent sample space so as to potentially capture topically useful and mutually independent properties of the original patient population. For scenarios where the prototypes are learned during the training process, this component may cause the prototypes to be spread out so as to not produce redundant prototypes which might not resemble and/or correctly capture the nuances and characteristics of real patients.

(4) Controlling for differential treatment remission prediction for a prototype. The differential prototype remission variance loss can be composed of both (I) the (inter) variance in remission predictions between different prototypes across all treatment types and (II) the (intra) variance within prototypes and between predictions of different treatments. These may be linearly combined through a weighted summation that allows for a customizable configuration between these loss components. Since the objective function may encourage greater variance across these two domains, this component of the loss function may be negated to induce that behavior during the training cycles.

A weighting coefficient may be assigned to each of the loss components defined above. For example the weighting coefficients may be as follows: (1) 1, (2) 0.01, (3.I) 0.001, (3.II) 0.01, (4) 0.01 [whose internal module coefficient composition may be (4.I) 0.05, (4.II) 0.95]. The performance of the classification problem, which is loss component (1) above, may be prioritized above all other loss components such as by assigning the largest weight to that component. The classification problem may be assigned the largest weight as this loss component corresponds to predicting the remission rates for each of the assigned drugs. By increasing the weight of this component, the accuracy of remission predictions by the MLA may be improved.

The weightings for the components (2) to (4) may affect how the patient samples are spread across the prototypes using the variance. The weightings for these components may be configured using trainable parameters. The values of these weightings may be continuously updated during the MLA training process in order to optimize the downstream objectives (e.g. supervised/unsupervised/reinforcement objectives as applied to mental health outcomes).

Training the MLA

The Adam optimizer may be used to dictate the training of the MLA and/or any other suitable optimizer may be used to train the MLA. The optimizer may use the final training dataset generated at step 315 to train the MLA. The optimizer may configure all trainable parameters of the MLA, such as the auto-encoder, the prototypes, and/or the predictive downstream layer(s). The optimizer may pass the data points from the final training dataset through the MLA, calculate the individual loss components for each data point, determine changes to be made to the parameters to minimize each of the loss components, and repeat this process to minimize the global loss.

The previously described loss components form a series of sub-optimization problems used by the global optimizer to determine if the existing parameters are optimally set so as to perform well at each of those sub-problems. The optimizer keeps track of each operation that takes place between each data and parameter so that for each training cycle, it can determine the proportional amount of changes to make to each independent parameter to minimize the downstream loss components. The proportion of changes that is done for each cycle of learning (otherwise known as the learning rate), is a hyperparameter that is set for the optimizer which affects the speed at which it can explore the plausible solution space to output an optimal MLA. The learning rate may be predetermined. For example, the learning rate may be set to 0.0001. This may optimize the results to ensure the MLA can learn differential treatment benefit.

Predicting a Treatment

Figure 4:
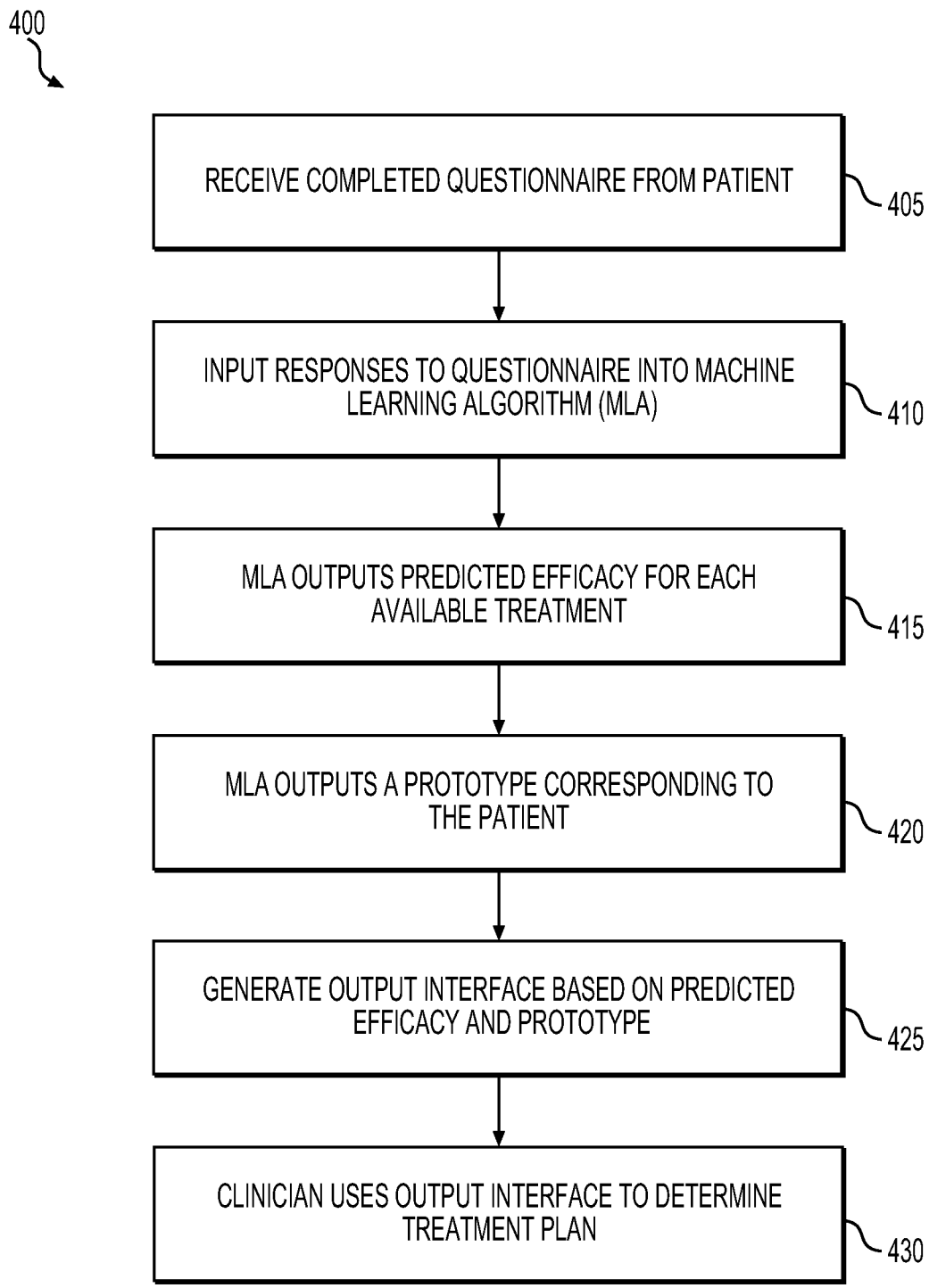
FIG. 4 illustrates a flow diagram of a method for predicting treatment efficacy in accordance with various embodiments of the present technology.

FIG. 4 illustrates a flow diagram of a method 400 for predicting treatment efficacy in accordance with various embodiments of the present technology.

At step 405 a completed questionnaire may be received by the processor, such as the processor 110. A questionnaire, such as the clinical questionnaire 210, may be administered over a digital platform and may consist of multiple choice questions, or free-text entry to provide answers. A questionnaire may be administered over a reoccurring interval or only once at the beginning of a treatment cycle. The completed questionnaire may have been completed by a patient, a clinician, and/or a caregiver/family member. The questionnaire may be completed while the patient is in a state of clinical depression or other mental illness or combination of comorbid illnesses, or retroactively. The patient's responses to questions in the questionnaire may be in a binary format (yes or no questions), categorical format (such as a rating from one to five), and/or any other format. The responses to the questionnaire may be normalized, such as by converting categorical responses to binary responses. The normalized responses may be stored in a vector and/or any other format for input to an MLA.

At step 410 the clinician may access the patient's profile, which may be linked to the patient's account. The patient's profile may be generated using their responses to the questionnaires described in the previous section. The patient's profile may use a variety of visualization methods to showcase the patient's answers and/or progress over time. The results of this questionnaire may be inputted into an MLA that outputs a predicted efficacy of one or more treatments, such as an MLA trained using the method 300 described above.

At step 415 the MLA may output a predicted efficacy of one or more treatments. The predicted efficacy of each treatment may indicate a predicted likelihood that the treatment will lead to remission if given to the patient. A treatment may include the name of an approved medication (e.g. sertraline) or an active drug prescribed to treat mental illness, such as major depression, and may include names of adjunctive medications for the treatment of mental illnesses (e.g. aripiprazole), as well as commonly used combinations of treatments (e.g. venlafaxine plus mirtazapine). A treatment may include psychotherapies (such as cognitive behavioral therapy) and/or neurostimulation (such as repetitive transcranial magnetic stimulation). The treatments may include dosages, which may be drawn from treatment guidelines and/or product monographs.

At step 420 the MLA may output a prototype corresponding to the patient. The prototype may be a predetermined prototype that is most similar to the patient's profile. The prototype may be encoded in the latent space, and a decoder may be used to generate a human-interpretable version of the prototype. The predicted efficacy of the one or more treatments and/or the prototype may be stored, such as in a memory of the computing environment 100.

At step 425 an interface may be generated based on the predicted efficacy of the one or more treatments and/or the prototype. The interface may be a user interface, a report, and/or any other type of interface. The interface may be output to a clinician treating the patient. FIGS. 5-9 illustrate examples of interfaces that may be output at step 425.

The interface may include a description of a prototypical patient that responds well to a given treatment based on the prototype determined at step 420. The data in the interface may be separated into categories based on statistics that relate to the population and/or statistics that relate to the individual patient. The interface may describe prototype and/or cluster focused statistics such as: features that correlate with a cluster (which in turn corresponds to a specific prototype), overall remission rates, or treatment variations, among others. The statistics that relate to the individual may describe the relationship between the patient relative to their closest prototypes or prototype-derived clusters or other patients who are also similar in nature to the same prototype.

The interface may include a list that indicates which prototype(s) the patient is most similar to, and/or a description of what each of those prototypes represent. The interface may include charts and/or graphs that plot the location of the patient relative to each of the prototypes in Euclidean or other space. A subset of points may be layered on top representing the underlying data to illustrate other similar patients in order to illustrate the distribution surrounding the various prototypes. The interfaces may allow the clinician to select various features to display in order to get a better sense of how one feature for a patient might be affecting their affinity to one prototype over another.

The interface may include an indication of the effects of symptom-based features and demographic-based features in determining the proximity of the patient to the set of prototypes. Rather than displaying all of the features used to generate the predictions in the interface, a subset of the features, such as a subset of related features, may be displayed.

At step 430 the clinician may use the interface to determine and/or confirm a treatment plan. Once the clinician has access to this information they may choose a treatment and/or prepare a treatment plan in collaboration with their patient. The clinician may input the treatment plan on the interface output at step 425, such as by selecting one or more treatments in the interface to generate the treatment plan.

Interfaces

FIG. 5 illustrates an exemplary interface 500 with patient prototypes in accordance with various embodiments of the present technology. The exemplary report 500 that may be output to a clinician along with the remission probability for each drug predicted by the system. The three prototypes A, B and C refer to prototypes discovered during MLA training and characterizing different segments of the patient population. The prototypes may have been generated during the training of the MLA and/or defined by a human operator.

The displayed distance measures, determined using the Frobenius norm, illustrate how far the patient is determined to be from each prototype. The determination may be made based on the patient's answers to the questionnaire. Visualizations based on these distances may provide the clinician an indication of how close the patient is to a given prototype.

The explanation tab explains, based on comparing patient features to prototype features, why the patient is closer or farther from a given prototype. Patients corresponding to the different prototypes may be more or less responsive to certain treatments. The explanations may help the clinician understand why the MLA might have predicted better or worse outcomes for a given treatment.

Figure 6:
FIG. 6 illustrates an exemplary interface with treatments in accordance with various embodiments of the present technology.

FIG. 6 illustrates an exemplary interface 600 with treatments in accordance with various embodiments of the present technology. The interface 600 includes a current treatment plan 610 listing treatments that are currently being used by the patient. The interface 600 includes a list of available treatments 620 that may be selected by the clinician to be added to the current treatment plan 610. The list of available treatments 620 may be displayed in a ranked order based on the predicted remission rates corresponding to each of the treatments. The clinician may select any of the available treatments to add to the current treatment plan 610 and/or a dosage for the selected treatment.

Figure 7:
FIG. 7 illustrates an exemplary interface with predicted remission rates in accordance with various embodiments of the present technology.

FIG. 7 illustrates an exemplary interface 700 with predicted remission rates in accordance with various embodiments of the present technology. The interface 700 includes patient information, current treatments that the patient is using, and dosage of those treatments for a patient. A predicted chance of remission is displayed for each of the current treatments. The predicted chance of remission may be determined using an MLA, such as the MLA generated by the method 300.

The interface 700 includes potential treatments that may be selected by the clinician to be added to the patient's treatment plan. The potential treatment includes a predicted chance of remission. The clinician may interact with the interface 700 to select any of the displayed treatments. The selected treatments may be incorporated into a treatment plan for the patient.

FIG. 8 illustrates an exemplary interface 800 for selecting treatments in accordance with various embodiments of the present technology. The interface 800 includes treatments that may be selected by a clinician. Each treatment includes information on the treatment, such as dosage information. A predicted probability of remission is included for each treatment, along with a difference between the predicted remission for the treatment and the patient's mean predicted probability of remission for all treatments. The clinician may select any of the treatments to generate a treatment plan for the patient.

Figure 9:
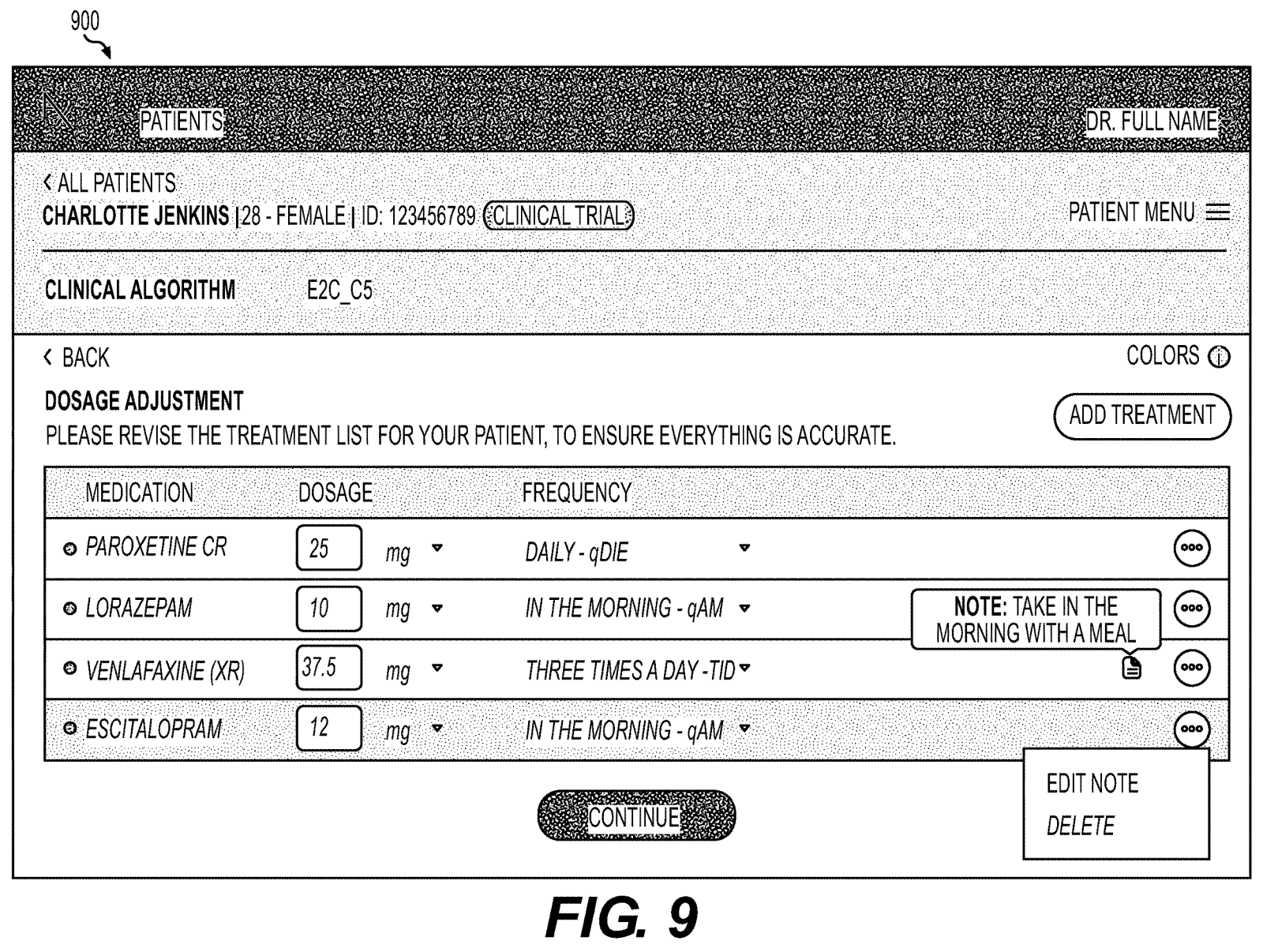

FIG. 9 illustrates an exemplary interface 900 for adjusting treatments in accordance with various embodiments of the present technology. The interface 900 includes treatments that have been selected by a clinician, such as treatments selected using the interfaces 600, 700, or 800. Using the interface 900, the clinician may select the dosage and/or frequency for each treatment. The clinician may select the amount of times per day that the treatment should be taken, a time of day that the treatment should be taken, number of days per week that the treatment should be taken, and/or any other frequency-related information. The clinician may input notes for each treatment.

While some of the above-described implementations may have been described and shown with reference to particular acts performed in a particular order, it will be understood that these acts may be combined, sub-divided, or re-ordered without departing from the teachings of the present technology. At least some of the acts may be executed in parallel or in series. Accordingly, the order and grouping of the act is not a limitation of the present technology.

The foregoing description is intended to be exemplary rather than limiting. Modifications and improvements to the above-described implementations of the present technology may be apparent to those skilled in the art.

The invention claimed is:

1. A system for predicting a treatment efficacy for a patient, the system comprising:
at least one processor, and memory storing a plurality of executable instructions which, when executed by the at least one processor, cause the system to:
train a machine learning algorithm (MLA) by:
receiving datasets from one or more sources corresponding to treatments for mental illness, wherein each data point in the datasets comprises questionnaire data corresponding to a patient and an indication of treatment efficacy corresponding to the respective patient;
normalizing results of the datasets, thereby generating normalized results;
generating, based on the normalized results, a training dataset;
selecting one or more features in the training dataset;
training, using the selected one or more features, the MLA to predict, for input patient data, an efficacy of each of a plurality of treatments; and
training the MLA to determine a prototype corresponding to the input patient data from a set of prototypes, wherein each prototype of the set of prototypes corresponds to a cluster of patient data, wherein the training is performed using a loss function, wherein the loss function determines a distance between prototypes, and wherein the loss function determines a variance in remission predictions between the prototypes,
predict the treatment efficacy for the patient by:
receiving questionnaire responses from the patient;
inputting the questionnaire responses into the MLA;
outputting, by the MLA, a predicted efficacy of each of the plurality of treatments for the patient; and
outputting, by the MLA, a prototype of the set of prototypes corresponding to the patient,
generate, based on the predicted efficacy of the one or more treatments and the prototype, an interface, and output for display the interface.

2. The system of claim 1, wherein the interface comprises, for each of the one or more treatments, a predicted likelihood of remission.

3. The system of claim 1, wherein the instructions further cause the system to receive, via the interface, user input indicating a treatment plan, wherein the treatment plan comprises at least one of the one or more treatments.

4. The system of claim 1, wherein the loss function is configured to increase the distance between prototypes and increase the variance in remission predictions between the prototypes.

5. The system of claim 1, wherein the prototype corresponding to the patient indicates a cluster of patients having similar features to the patient, wherein the interface provides an indication of a similarity between the patient and the cluster of patients, and wherein the interface explains how the prototype relates to the predicted efficacy.

6. The system of claim 1, wherein the MLA comprises a neural network, wherein the prototype is determined by a layer of the neural network corresponding to prototypes, and wherein the layer of the neural network corresponding to prototypes outputs a distance between the patient and each prototype of the set of prototypes.

7. A system comprising:
at least one processor, and memory storing a plurality of executable instructions which, when executed by the at least one processor, cause the system to:
receive questionnaire responses from a patient requiring treatment;
input the questionnaire responses into a machine learning algorithm (MLA), wherein the MLA was trained based on labelled patient data, wherein each data point in the labelled patient data comprises questionnaire data corresponding to a respective patient and a label indicating an efficacy of a treatment for the respective patient, and wherein the MLA is configured to generate a set of prototypes based on the labelled patient data;
receive, from the MLA, a predicted efficacy of one or more treatments for the patient;
receive, from the MLA, a prototype of the set of prototypes corresponding to the patient;
generate, based on the predicted efficacy of the one or more treatments and the prototype, an interface; and
output for display the interface.

8. The system of claim 7, wherein the interface comprises:
a predicted likelihood of remission for each of the one or more treatments, and
an indication of a distance between the patient and the prototype.

9. The system of claim 7, wherein each prototype of the set of prototypes corresponds to a cluster of patients generated from the labelled patient data.

10. The system of claim 7, wherein the MLA comprises a neural network, and wherein the prototype is determined by a layer of the neural network corresponding to prototypes.

11. The system of claim 10, wherein the layer of the neural network corresponding to prototypes outputs a distance between the patient and each prototype of the set of prototypes.

12. A system for training a machine learning algorithm (MLA), the system comprising:
at least one processor, and memory storing a plurality of executable instructions which, when executed by the at least one processor, cause the system to:
receive datasets from one or more sources corresponding to treatments for mental illness, wherein each data point in the datasets comprises questionnaire data corresponding to a patient and an indication of treatment efficacy corresponding to the respective patient;

normalize results of the datasets, thereby generating normalized results;

generate, based on the normalized results, a training dataset;

select one or more features in the training dataset;

train, using the selected one or more features, the MLA to predict, for input patient data, an efficacy of each of the treatments; and train the MLA to determine a prototype corresponding to the input patient data from a set of prototypes, wherein each prototype of the set of prototypes corresponds to a cluster of patient data, wherein the training is performed using a loss function, wherein the loss function determines a distance between prototypes of the set of prototypes, and wherein the loss function determines a variance in remission predictions between the prototypes of the set of prototypes.

13. The system of claim 12, wherein the instructions that cause the system to train the MLA to determine a prototype corresponding to the input patient data comprise instructions that cause the system to train the MLA based at least in part on a prototype sample distance variance.

14. The system of claim 12, wherein the instructions further cause the system to determine a prototype sample distance variance based at least in part on a variance of distances between a set of nearest samples for a given prototype and the given prototype itself.

15. The system of claim 12, wherein the instructions further cause the system to determine a prototype sample distance variance based at least in part on variance of pairwise distances between the set of prototypes.

16. The system of claim 12, wherein the instructions further cause the system to determine a prototype remission prediction based at least in part on variance of differential remission predictions for the set of prototypes across a treatment type.

17. The system of claim 12, wherein the instructions further cause the system to determine a prototype remission prediction based at least in part on variance of differential remission predictions for a given prototype across a plurality of treatment types.

18. The system of claim 12, wherein the training is performed using a loss function, wherein the loss function determines a difference between a predicted likelihood of remission and a labeled occurrence of remission, wherein the loss function determines an autoencoder loss indicating a distance between an original sample and a decoded sample, and wherein the loss function is configured to increase the distance between prototypes and increase the variance in remission predictions between the prototypes.

19. The system of claim 12, wherein the instructions that cause the system to normalize the results of the datasets comprise instructions that cause the system to group questions in different datasets relating to a same feature.

20. The system of claim 12, wherein the instructions that causse the system to normalize the results of the datasets comprise instructions that cause the system to convert categorical responses in the datasets to binary responses.

* * * * *